(12) United States Patent
Chakraborty

(10) Patent No.: US 11,672,454 B2
(45) Date of Patent: Jun. 13, 2023

(54) APPARATUS AND METHOD FOR USER STRESS MONITORING

(71) Applicant: Soumik Chakraborty, Portland, OR (US)

(72) Inventor: Soumik Chakraborty, Portland, OR (US)

(*) Notice: Subject to any disclaimer, the term of this patent is extended or adjusted under 35 U.S.C. 154(b) by 94 days.

(21) Appl. No.: 16/928,717

(22) Filed: Jul. 14, 2020

(65) Prior Publication Data

US 2022/0015675 A1  Jan. 20, 2022

(51) Int. Cl.
| | |
|---|---|
| A61B 5/16 | (2006.01) |
| A61B 5/0205 | (2006.01) |
| A61B 5/00 | (2006.01) |
| A61B 5/117 | (2016.01) |
| A61B 5/0533 | (2021.01) |
| A61B 5/021 | (2006.01) |
| A61B 5/024 | (2006.01) |

(52) U.S. Cl.
CPC .............. *A61B 5/165* (2013.01); *A61B 5/002* (2013.01); *A61B 5/0004* (2013.01); *A61B 5/0205* (2013.01); *A61B 5/117* (2013.01); *A61B 5/6807* (2013.01); *A61B 5/746* (2013.01); *A61B 5/021* (2013.01); *A61B 5/02438* (2013.01); *A61B 5/0533* (2013.01)

(58) Field of Classification Search
CPC ....... A61B 5/165; A61B 5/0004; A61B 5/002; A61B 5/0205; A61B 5/117; A61B 5/6807; A61B 5/746; A61B 5/021; A61B 5/02438; A61B 5/0533

See application file for complete search history.

(56) References Cited

U.S. PATENT DOCUMENTS

| | | | | |
|---|---|---|---|---|
| 6,024,575 | A * | 2/2000 | Ulrich | A43B 17/00 434/262 |
| 10,964,421 | B2 * | 3/2021 | Lane | A61B 5/6846 |
| 11,052,286 | B2 * | 7/2021 | Reddy | A63B 24/0006 |
| 2017/0112434 | A1 * | 4/2017 | Lane | A61B 5/6846 |
| 2018/0169474 | A1 * | 6/2018 | Reddy | A63B 24/0062 |
| 2019/0090812 | A1 * | 3/2019 | Martin | G06F 1/3231 |

* cited by examiner

*Primary Examiner* — Jonathan T Kuo
(74) *Attorney, Agent, or Firm* — Mohr IP Law Solutions, PC

(57) ABSTRACT

A system and method for monitoring user stress levels is provided. One embodiment measures blood pressure using a blood pressure monitor in a monitoring sock; measures heart rate of the user using a heart rate monitor in the monitoring sock; monitors galvanic skin response (GSR) of the foot using at least one electrode in a monitoring shoe that is being worn by the user; generates supplemental information that includes at least a date and time of acquisition of the received blood pressure data, the heart rate data, and/or the GSR data; communicates the supplemental information, the blood pressure the heart rate data, and the GSR data; and stores the supplemental information, the blood pressure data, the heart rate data, and the GSR data into a memory.

18 Claims, 5 Drawing Sheets

APPARATUS AND METHOD FOR USER STRESS MONITORING

BACKGROUND OF THE INVENTION

In the arts of monitoring biometrics of a person for health monitoring purposes, and in particular monitoring biometrics for determination of user stress levels, various user biometric monitoring devices have been contemplated. However, such legacy user biometric monitoring devices can be cumbersome, intrusive, and difficult to use by the person who must secure such legacy user biometric monitoring devices to their body for real-time biometric monitoring.

Accordingly, in the arts of user biometric monitoring devices for determination of user stress levels, there is a need in the arts for improved methods, apparatus, and systems for monitoring the biometrics of a user in real-time.

SUMMARY OF THE INVENTION

Embodiments of the electronic device use history system provide a system and method for monitoring stress of a user in real time. One embodiment measures blood pressure using a blood pressure monitor in a monitoring sock; measures heart rate of the user using a heart rate monitor in the monitoring sock; monitors galvanic skin response (GSR) of the foot using at least one electrode in a monitoring shoe that is being worn by the user; generates supplemental information that includes at least a date and time of acquisition of the received blood pressure data, the heart rate data, and/or the GSR data; communicates the supplemental information, the blood pressure data, the heart rate data, and the GSR data; and stores the supplemental information, the blood pressure data, the heart rate data, and the GSR data into a memory.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
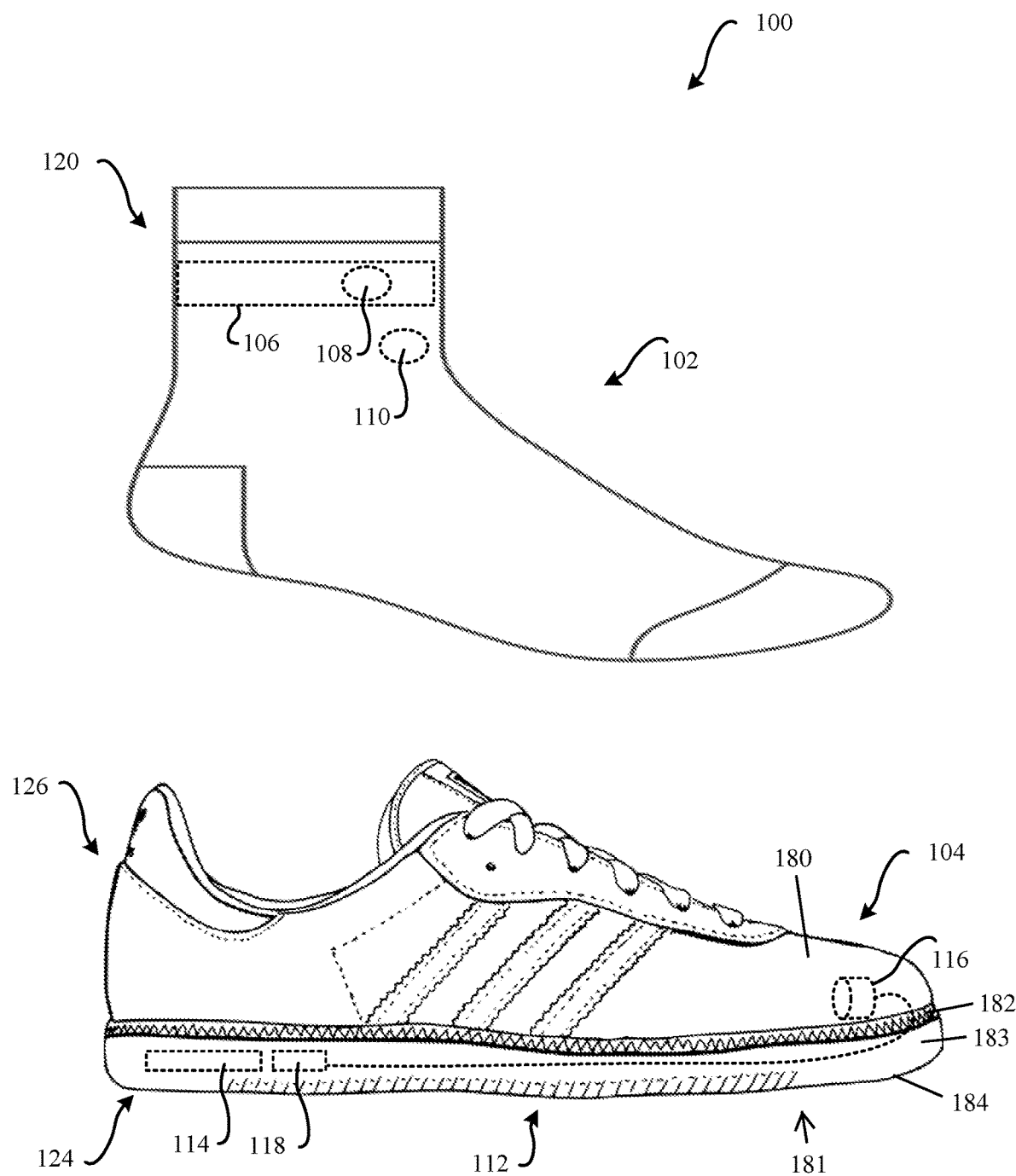
FIG. 1 is a diagram of a user stress level monitoring system embodiment in a monitoring sock and a monitoring shoe.
Figure 2:
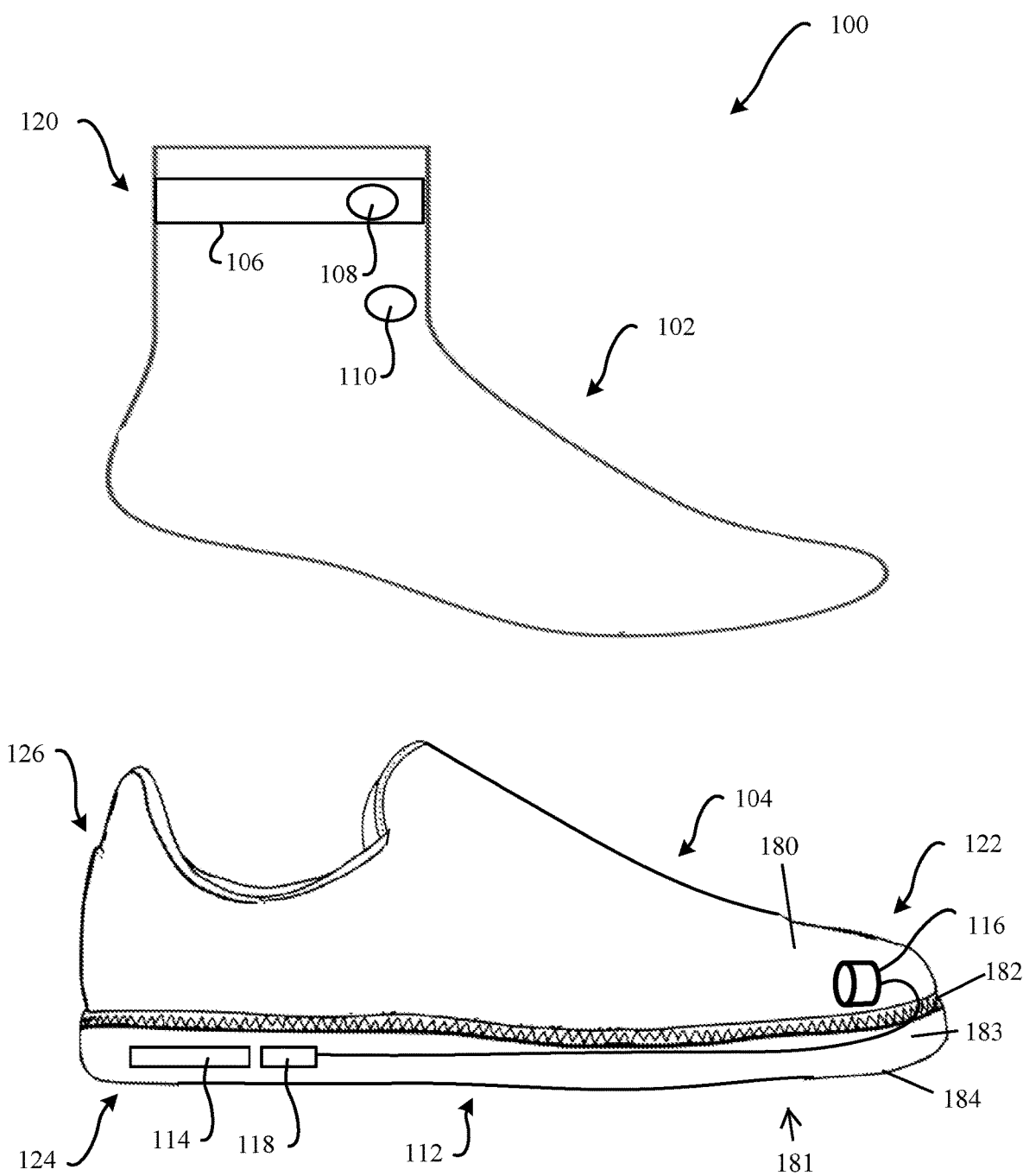
FIG. 2 is a cut-away diagram of the monitoring sock and a monitoring shoe.

FIG. 1 is a diagram of a user stress level monitoring system 100 embodiment in a monitoring sock 102 and a monitoring shoe 104. FIG. 2 is a cut-away diagram of the monitoring sock 102 and a monitoring shoe 104.

The disclosed systems and methods for securing a user stress level monitoring system 100 will become better understood through review of the following detailed description in conjunction with the figures. The detailed description and figures provide examples of the various inventions described herein. Those skilled in the art will understand that the disclosed examples may be varied, modified, and altered without departing from the scope of the inventions described herein. Many variations are contemplated for different applications and design considerations, however, for the sake of brevity, each and every contemplated variation is not individually described in the following detailed description.

Throughout the following detailed description, a variety of examples for systems and methods the user stress level monitoring system 100 are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components.

"Communicatively coupled" means that an electronic device is communicatively connected to another electronic device, either wirelessly or with a wire based connector, whether directly or indirectly through a communication system.

An unexpected benefit is that the components of the user stress level monitoring system 100 may be hidden from view to support non-intrusive health monitoring of a user. Further, the user stress level monitoring system 100 may be conveniently and comfortably worn by the user for long durations. Accordingly, the various embodiments of the user stress level monitoring system 100 may collect stress data at any time that the user is wearing the monitoring sock 102 and/or the monitoring shoe 104. Another further unexpected benefit of monitoring stress level at the user's foot, and in particular monitoring blood pressure at the use's foot, is that blocked leg arteries and/or peripheral artery disease may be more readily detected. Further, a plurality of different monitoring socks 102, with different colors and/or styles, may be configured to cooperatively work with a plurality of different monitoring shoes 104 of different colors and/or styles.

Returning to the non-limiting example embodiment of FIG. 1, the monitoring sock 102 comprises a blood pressure monitor 106, a heart rate monitor 108, and a wireless transceiver 110. The monitoring shoe 104 comprises a galvanic skin response (GSR) monitor 112 and a stress level monitoring processor system 114. The GSR monitor 112 comprises one or more electrodes 116 and a GSR monitoring processor 118. The wireless transceiver 110, interchangeably referred to herein as the monitoring sock wireless transceiver 110, communicatively couples the blood pressure monitor 106 and the heart rate monitor 108 to the stress level monitoring processor system 114. Examples of the blood pressure monitor 106 include a blood pressure meter, gauge and/or sphygmomanometer. The wireless transceiver 110 receives blood pressure data from the blood pressure monitor 106 and receives heart rate data from the heart rate monitor 108, and then outputs a wireless signal with the received blood pressure data and heart rate data.

In a preferred embodiment, the example heart rate monitor 108, the blood pressure monitor 106, and/or the wireless transceiver 110 are collocated near the cuff 120 of the monitoring sock 102 which, when the monitoring sock 102 is worn by the user, would be at a predefined location above the ankle of the foot of the user. In an example embodiment, the blood pressure monitor 106, the heart rate monitor 108, and/or the wireless transceiver 110 are integrated together into a single unit. In another embodiment, the blood pressure monitor 106, the heart rate monitor 108, and/or the wireless transceiver 110 may be separate components. The blood pressure monitor 106, the heart rate monitor 108, and/or the wireless transceiver 110 may be integrated into (woven into) the fabric of the monitoring sock 102. In another embodiment, the blood pressure monitor 106, the heart rate monitor 108, and/or the wireless transceiver 110 may be separately sewn into the interior region of the monitoring sock 102 near the cuff 120. Alternatively, or additionally, the blood pressure monitor 106, the heart rate monitor 108, and/or the wireless transceiver 110 may be secured to the monitoring sock 102 using a suitable adhesive or a hook and loop fabric. Any suitable blood pressure monitor 106, heart rate monitor 108, and/or wireless transceiver 110 now known or later developed may be used in the various embodiments of the user stress level monitoring system 100.

By collocating the blood pressure monitor 106 and the heart rate monitor 108, or locating the blood pressure monitor 106 and the heart rate monitor 108 in close proximity to each other, information corresponding to the monitored blood pressure (blood pressure data) and information corresponding to the heart rate (heart rate data) of the user may be more easily communicated by the wireless transceiver 110 to the stress level monitoring processor system 114. In other embodiments, the heart rate monitor 108 may be located in any other suitable location in the monitoring sock 102, preferably at a location that is comfortable for the user who is wearing the monitoring sock 102. In a preferred embodiment, the blood pressure monitor 106 and the heart rate monitor 108 are communicatively connected to the wireless transceiver 110 using a wire-based connector. In other embodiments, the blood pressure monitor 106 and/or the heart rate monitor 108 are wirelessly communicatively coupled to the wireless transceiver 110. One or more small power sources (not shown), such as a battery, may reside in the monitoring sock 102 or within the blood pressure monitor 106, the heart rate monitor 108, and/or the wireless transceiver 110, to power these components.

In a preferred embodiment, the one or more electrodes 116 are located in a toe 122 of the monitoring shoe 104. The one or more electrodes 116 are configured to measure or detect the skin resistivity, or changes in skin resistivity, at the toes of the user wearing the monitoring shoe 104. However, the one or more electrodes 116 may be located in any suitable location within the monitoring shoe 104 in alternative embodiments. An unexpected benefit of locating the electrodes 116 in the monitoring shoe 104 is that the user's feet tend to sweat more than the user's fingers, hands, or other body parts. Accordingly, the effectiveness of the one or more electrodes 116 is increased when sensing resistivity changes at the user's foot.

The stress level monitoring processor system 114 and the GSR monitoring processor 118 are preferably located in the heel 124 below a backstay 126 of the monitoring shoe 104. A shoe heel is known to be relatively thick. Accordingly, there is sufficient space within the interior of the heel 124 of the monitoring shoe 104 to accommodate the stress level monitoring processor system 114 and the GSR monitoring processor 118 without creating discomfort to the user wearing the monitoring shoe 104. One or more small power sources (not shown), such as a battery, may reside in the monitoring shoe 104 or within the stress level monitoring processor system 114 and/or the GSR monitoring processor 118 to power these components.

In a preferred embodiment, the GSR monitoring processor 118 is communicatively connected to the stress level monitoring processor system 114 using a wire-based connector. In other embodiments, the GSR monitoring processor 118 is wirelessly communicatively coupled to the stress level monitoring processor system 114. The GSR monitoring processor 118 receives a GSR signal that is output from the electrodes 116. The GSR monitoring processor 118 then generates and outputs GSR data corresponding to the detected GSR of the user to the stress level monitoring processor system 114.

Figure 3:
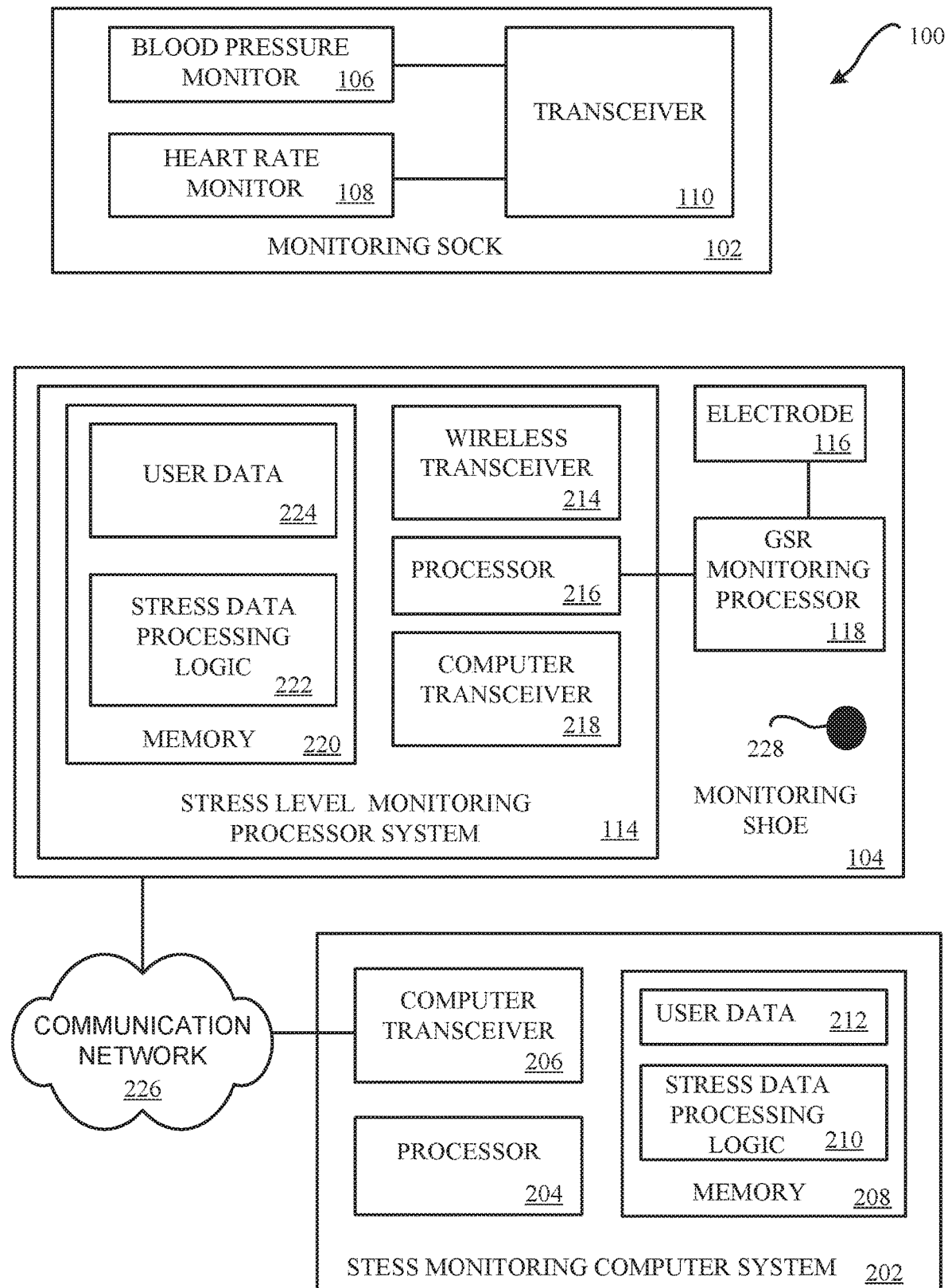
FIG. 3 is a block diagram of the user stress level monitoring system.

FIG. 3 is a block diagram of the user stress level monitoring system 100. The user stress level monitoring system 100 comprises the monitoring sock 102 and the monitoring shoe 104, and further comprises the stress monitoring computer system 202. The stress monitoring computer system 202 comprises a processor 204, a computer transceiver 206, and a memory 208. The memory 208 comprises portions for storing the stress data processing logic 210 and user data 212. In some embodiments, the stress data processing logic 210 may be integrated with other logic. In other embodiments, some or all of these memory and other data manipulation functions may be provided by using a remote server or other electronic devices suitably connected via the Internet or otherwise to a client device. Other embodiments of the stress monitoring computer system 202 may include some, or may omit some, of the above-described media processing components. Further, additional components not described herein may be included in alternative embodiments.

The stress level monitoring processor system 114 comprises a wireless transceiver 214, a processor 216, a computer transceiver 218, and a memory 220. The memory 220 comprises portions for storing the stress data processing logic 222 and user data 224. In some embodiments, the stress data processing logic 222 may be integrated with other logic. In other embodiments, some or all of these memory and other data manipulation functions may be provided by using a remote server or other electronic devices suitably connected via the Internet or otherwise to a client device. Other embodiments of the stress monitoring computer system 202 may include some, or may omit some, of the above-described media processing components. Further, additional components not described herein may be included in alternative embodiments.

In practice, while the use is wearing the monitoring sock 102 and/or the monitoring shoe 104, the blood pressure monitor 106 measures the user's blood pressure. The blood pressure monitor 106 generates and communicates a blood pressure information signal with blood pressure data to the transceiver 110. Concurrently, the heart rate monitor measures the user's heart rate, and generates and communicates a heart rate information signal with heart rate data to the transceiver 110. The transceiver 110 then communicates an output signal with the received blood pressure data and heart rate data to the wireless transceiver 214 residing in the monitoring shoe 104.

Concurrently, the one or more electrodes 116 are detecting resistivity, or changes in resistivity, at the surface of the user's toe (or in another portion of the user's foot that is in proximity to the electrodes 116). A resistivity signal with resistivity information is communicated from the one or more electrodes 116 to the GSR monitor 112. The GSR monitor 112 converts the received resistivity signal with resistivity information into GSR data that is then communicated as a signal to the processor 216 in the stress level monitoring processor system 114. In some embodiments, the GSR monitor 112 may be incorporated into the stress level monitoring processor system 114 as an integrated component and/or may be implemented as software of the stress data processing logic 222.

The processor 216, executing the stress data processing logic 222, processes the received blood pressure data, the received heart rate data, the received GSR data, and suitable supplemental information into user data. The user data is stored into the user data 224 portion of memory 220. Over time, some amount of user data is acquired and stored into the user data 224.

The supplemental information may include any suitable supplemental information of interest. For example, the supplemental information may include the date and time of acquisition of the user data. Additionally, identifier information that identifies the user, and/or that identifies the stress level monitoring processor system 114, that identifies the monitoring sock 102, that identifies the monitoring shoe 104, and/or that identifies the components therein, may be included in the supplemental information.

The transceiver 110 and the wireless transceiver 214 are operable to communicate with each other using a low power wireless signal. A non-limiting exemplary low power wireless signal is the well-known Bluetooth signal. Any suitable wireless signal format now known or later developed may be used by the various embodiments. The wireless transceiver 214 may be configured to pair with a plurality of different transceivers 110 such that the use may wear a plurality of different monitoring socks 102 depending on the particular activity that the user is doing. Further, a plurality of different monitoring shows 104, each with their own wireless transceiver 214, can be configured to pair with any of the transceivers 110 in the different monitoring socks 102.

By storing the acquired user data over some duration (period of time), the user is able to go about their ordinary daily routine. For example, the user may go to work, run errands, or even go to the gym for exercise. That is, embodiments of the user stress level monitoring system 100 are able to acquire the user data at any time on a real-time basis.

From time to time, the stored user data and supplemental information is retrieved from the user data 224 by the processor 216. The processor 216 formats the retrieved user data and supplemental information into a data signal that is communicated from the computer transceiver 218 to the computer transceiver 206 residing in the stress monitoring computer system 202, via the intervening communication network 226. The processor 204, executing the stress data processing logic 210, analyzes the received user data and supplemental information to determine user stress levels. Further analysis of the user stress levels may indicate that the user may be experiencing undesirable health effects caused by over stress or over stressful situations.

The communication network 226 is illustrated as a generic communication system. In one embodiment, the communication network 226 comprises a cellular telephone system, such as a radio frequency (RF) wireless system. Alternatively, the communication network 226 may be a telephony system, the Internet, a Wi-fi system, a microwave communication system, a fiber optics system, an intranet system, a local access network (LAN) system, an Ethernet system, a cable system, a radio frequency system, a cellular system, an infrared system, a satellite system, or a hybrid system comprised of multiple types of communication media. Additionally, embodiments of the user stress level monitoring system 100 may be implemented to communicate using other types of communication technologies, such as but not limited to, digital subscriber loop (DSL), X.25, Internet Protocol (IP), Ethernet, Integrated Services Digital Network (ISDN) and asynchronous transfer mode (ATM). Also, embodiments of the user stress level monitoring system 100 may be configured to communicate over combination systems having a plurality of segments which employ different formats for each segment that employ different technologies on each segment.

In an alternative embodiment, the wireless transceiver 214 and the computer transceiver 218 are replaced with a single transceiver that is operable to wirelessly receive information from the transceiver 110 and to wirelessly transmit the acquired user data to the computer transceiver 206. For example, if the single transceiver is a Bluetooth or the like transceiver, the single transceiver may detect when the stress level monitoring processor system 114 comes into close proximity to the stress monitoring computer system 202. In response to detecting the close proximity, the single transceiver may initiate a pairing process with the computer transceiver 206, and then transfer the user data over to the stress monitoring computer system 202. Alternatively, or additionally, the single transceiver may periodically transmit an announcement. When the announcement is heard by the computer transceiver 206, a pairing process can be initiated for downloading the acquired user data.

The received user data is stored into the user data 212 portion of the memory 208 of the stress monitoring computer system 202. Accordingly, over long periods of time, a relatively large amount of user data can be accumulated for stress analysis.

The stress data processing logic 210, when executed by processor 210, may then from time to time, or under the direction of an operator, retrieve the acquired user blood pressure data, heart rate data and GSR data to computationally determine the user's stress level at the time that the data was acquired. Further analysis, as is known in the arts, may be used to analyze the user data over time so as to assess the stress levels, and therefore infer the user's health, from the acquired user data. In a preferred embodiment, ensemble machine learning models may be trained and tested with time-series data corresponding to the user's health data profile to detect and/or to identify potential stress related health problems in the user.

Preferably, the stress monitoring computer system 202 is able to receive user data from a plurality of different individuals. Accordingly, a plurality of doctors may monitor stress levels for a plurality of patients.

Alternatively, or additionally, functions of the stress data processing logic 210 may be incorporated into the stress data processing logic 222. In such embodiments, the user stress level monitoring system 100 may detect a serious or life threatening condition and then emit an alarm to the user from an optional alarm indicating device 228 alarm if the stress level of the user becomes unhealthy. For example, but not limited to, the alarm indicating device 228 may be a light indicator that outputs a visible light to indicate stress level information and/or the alarm condition. Alternatively, or additionally, the alarm indicating device 228 may be a speaker or the like that outputs an audible sound to indicate the stress level information and/or the alarm condition. Alternatively, or additionally, the wireless transceiver 214 may generate and communicate an alarm condition to a device of the user, such as their smart phone or the like.

In some embodiments, the stress data processing logic 222 may be configured to generate stress analysis reports on a real-time basis. The generated stress analysis reports may then be generated and communicated from the wireless transceiver 214. The report data may be received by a device of the user, such as their smart phone or the like. Accordingly, the user would have access to stress level reports on a real-time basis.

Figure 4:
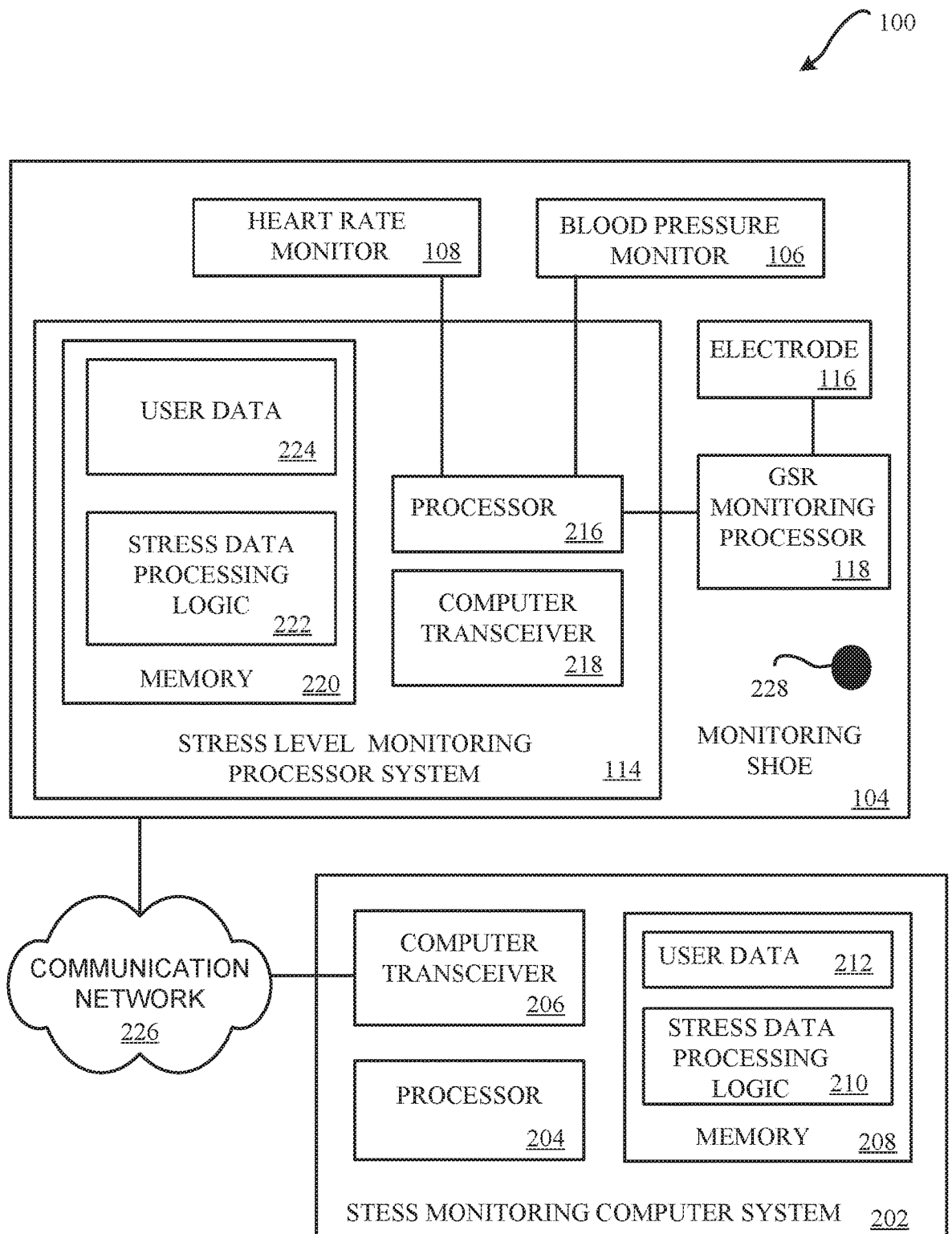
FIG. 4 is a block diagram of an alternative embodiment of the user stress level monitoring system.

FIG. 4 is a block diagram of an alternative embodiment of the user stress level monitoring system where the blood pressure monitor 106, the heart rate monitor 108, the electrode 116, and the GSR monitoring processor 118 are located in the monitoring shoe 104. In this embodiment, the monitoring sock 102 is omitted since all components are located in the monitoring shoe 104. Further, the wireless transceivers 110, 214 are omitted. For example, but not limited to, the blood pressure monitor 106 and/or the heart rate monitor 108 may be in the inner portion or lining of the backstay of the monitoring shoe 104.

Figure 5:
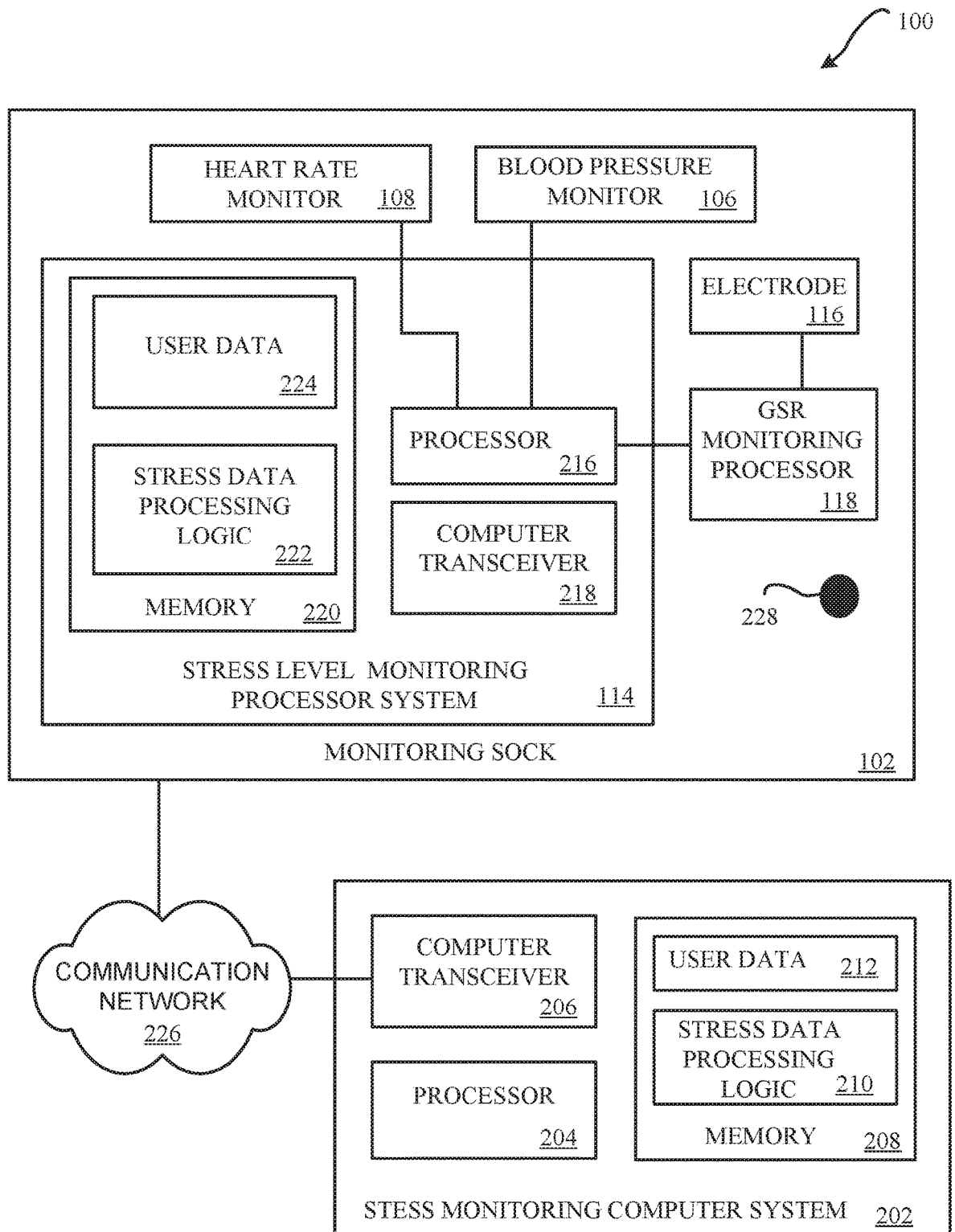
FIG. 5 is a block diagram of an alternative embodiment of the user stress level monitoring system.

FIG. 5 is a block diagram of an alternative embodiment of the user stress level monitoring system where the blood pressure monitor 106, the heart rate monitor 108, the electrode 116, and the GSR monitoring processor 118 are located in the monitoring sock 102. In this embodiment, the monitoring shoe 104 is omitted since all components are located in the monitoring sock 102. Further, the wireless transceivers 110, 214 are omitted.

Other embodiments have a selected one of the blood pressure monitor 106 or the heart rate monitor 108 in the monitoring sock 102, while the other component resides in the monitoring shoe 104.

It should be emphasized that the above-described embodiments of the electronic device use history system 100 are merely possible examples of implementations of the invention. Many variations and modifications may be made to the above-described embodiments. All such modifications and variations are intended to be included herein within the scope of this disclosure and protected by the following claims.

Furthermore, the disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower, or equal in scope to the original claims, are to be considered within the subject matter of the inventions described herein.

Therefore, having thus described the invention, at least the following is claimed:

1. A user stress level monitoring system, comprising:
   a monitoring sock configured to be placed over a foot of a user, comprising:
      a blood pressure monitor integrated within the material of the sock that measures blood pressure of the user above an ankle of a foot of the user and that outputs blood pressure data corresponding to the measured blood pressure of the user; and
      a heart rate monitor integrated within the material of the sock that measures a heart rate of the user at the foot of the user and that outputs heart rate data corresponding to the measured heart rate of the user;
   a monitoring shoe configured to receive the foot disposed within the monitoring sock, the monitoring shoe comprising:
      at least one electrode integrated within the material of the shoe and configured to monitor galvanic skin response (GSR) of the foot disposed in the monitoring sock from a position outside the monitoring sock when the foot disposed in the monitoring sock is received in the monitoring shoe and that outputs a GSR measurement signal; and
      a GSR monitoring processor communicatively coupled to the at least one electrode, that receives the GSR measurement, and that converts the received GSR measurement signal into GSR data;
   a stress level monitoring processor system communicatively coupled to the blood pressure monitor, the heart rate monitor, and the GSR monitoring processor, comprising:
      a memory; and
      a processor,
   wherein the processor generates supplemental information that includes at least one of a date and time of acquisition of at least one of the received blood pressure data, the received heart rate data, and the received GSR data, and
   wherein the processor stores the received blood pressure data, the received heart rate data, the received GSR data, and the supplemental information into the memory.

2. The user stress level monitoring system of claim 1, wherein the at least one electrode is integrated within and located at a toe of the monitoring shoe outside the monitoring sock when the foot disposed within the monitoring sock is received in the monitoring shoe and is configured to detect the GSR of a toe of the user disposed within the monitoring sock.

3. The stress level monitoring system of claim 1, wherein the monitoring sock further comprises:
   a monitoring sock wireless transceiver that is communicatively coupled to the blood pressure monitor and the heart rate monitor, wherein the monitoring sock wireless transceiver outputs a wireless signal with the blood pressure data and the heart rate data.

4. The stress level monitoring system of claim 3, wherein the monitoring shoe further comprises:
a monitoring shoe wireless transceiver,
wherein the monitoring shoe wireless transceiver receives the wireless signal with the blood pressure data and the heart rate data output by the monitoring sock wireless transceiver.

5. The stress level monitoring system of claim 4, wherein the monitoring shoe transceiver outputs a wireless signal with the blood pressure data, the heart rate data, the GSR data and the supplemental information to a stress monitoring computer system.

6. The stress level monitoring system of claim 5, wherein the supplemental information further comprises information that identifies at least one of the user and the stress level monitoring processor system, and wherein the stress monitoring computer system comprises:
a memory,
wherein the received user data is stored in the memory with user data for a plurality of other users.

7. The stress level monitoring system of claim 1, wherein at least one of the blood pressure monitor and the heart rate monitor are located in a cuff of the monitoring sock.

8. The stress level monitoring system of claim 1, wherein the stress level monitoring processor system is located in a heel of the monitoring shoe.

9. The stress level monitoring system of claim 1, wherein the GSR monitoring processor is located in a heel of the monitoring shoe.

10. The stress level monitoring system of claim 1, wherein the GSR monitoring processor is a component of the stress level monitoring processor system.

11. The stress level monitoring system of claim 1, wherein the monitoring shoe further comprises:
a computer transceiver,
wherein the computer transceiver outputs user data with the blood pressure data, the heart rate data, the GSR data and the supplemental information to a communication network, and
wherein a stress monitoring computer system receives the user data from the communication network.

12. The stress level monitoring system of claim 11, wherein the supplemental information further comprises information that identifies at least one of the user and the stress level monitoring processor system, and wherein the stress monitoring computer system comprises:
a memory,
wherein the received user data is stored in the memory with user data for a plurality of other users.

13. The stress level monitoring system of claim 11, wherein the stress level monitoring processor system further comprises:
stress data processing logic that is executed by the processor and that determines a stress level of the user.

14. The stress level monitoring system of claim 13, wherein the monitoring shoe further comprises:
an alarm indicating device that outputs an alarm if the stress level of the user becomes unhealthy.

15. A method of monitoring user stress levels, comprising:
measuring blood pressure of a user using a blood pressure monitor integrated within the shoe and that is disposed in at least one of a cuff of a monitoring sock that is being worn by the user and a backstay of a monitoring shoe that is being worn by the user, wherein the blood pressure monitor is located above an ankle of a foot of the user and that outputs blood pressure data corresponding to the measure blood pressure of the user;
measuring a heart rate of the user using a heart rate monitor that is integrated within the shoe and disposed in at least one of a cuff of a monitoring sock and a backstay of a monitoring shoe that is being worn by the user, wherein the heart rate monitor outputs heart rate data corresponding to the measured heart rate of the user;
monitoring galvanic skin response (GSR) of the foot using at least one electrode that is fixedly integrated within the shoe outside of a sock or a monitoring sock being worn by the user and outputs a GSR measurement signal, wherein the at least one electrode resides in the monitoring shoe that is being worn by the user;
receiving the GSR measurement at GSR monitoring processor that is communicatively coupled to the at least one electrode, wherein the GSR monitoring processor converts the received GSR measurement signal into GSR data;
communicating the blood pressure data, the heart rate data, and the GSR data to a stress level monitoring processor system that is communicatively coupled to the blood pressure monitor, the heart rate monitor, and the GSR monitoring processor;
generating, at the stress level monitoring processor, supplemental information that includes at least one of a date and a time of acquisition of the received blood pressure data, the received heart rate data, and the received GSR data; and
storing the received blood pressure data, the received heart rate data, the received GSR data, and the supplemental information into a memory.

16. The method of claim 15, wherein the monitoring sock comprises a monitoring sock wireless transceiver that is communicatively coupled to the at least one of the blood pressure monitor and the heart rate monitor residing in the monitoring sock, and further comprising:
outputting a wireless signal from the monitoring sock wireless transceiver with at least one of the blood pressure data and the heart rate data,
wherein the stress level monitoring processor system receives the wireless signal.

17. The method of claim 15, wherein the at least one of the blood pressure monitor and the heart rate monitor are integrated in a cuff of the monitoring sock, wherein the stress level monitoring processor system is integrated in a heel of the monitoring shoe, wherein the GSR monitoring processor is integrated in a heel of the monitoring shoe, and wherein the at least one electrode is integrated in a toe of the monitoring shoe.

18. The method of claim 15, further comprising:
outputting a wireless signal from a monitoring shoe transceiver located in the monitoring shoe to a stress monitoring computer system, wherein the wireless signal includes the blood pressure data, the heart rate data, the GSR data and the supplemental information.

* * * * *